(12) United States Patent  
Ehrenfreund et al.

(10) Patent No.: US 8,357,816 B2  
(45) Date of Patent: Jan. 22, 2013

(54) CHEMICAL COMPOUNDS

(75) Inventors: Josef Ehrenfreund, Basel (CH); Pierre Joseph Marcel Jung, Basel (CH); Hans Tobler, Basel (CH); Harald Walter, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 12/841,586

(22) Filed: Jul. 22, 2010

(65) Prior Publication Data

US 2010/0305351 A1    Dec. 2, 2010

Related U.S. Application Data

(62) Division of application No. 10/509,607, filed as application No. PCT/IB03/01110 on Mar. 21, 2003, now Pat. No. 7,767,623.

(30) Foreign Application Priority Data

Mar. 27, 2002    (GB) .................................. 0207253.6

(51) Int. Cl.  
*C07F 7/10* (2006.01)
(52) U.S. Cl. ..................................................... 556/413
(58) Field of Classification Search ................... 544/242; 546/315, 316; 556/413  
See application file for complete search history.

(56) References Cited

U.S. PATENT DOCUMENTS

| | | | |
|---|---|---|---|
| 6,747,047 B2 | 6/2004 | Lahm et al. | |
| 6,995,178 B2 | 2/2006 | Lahm et al. | |
| 7,338,978 B2 | 3/2008 | Lahm et al. | |
| 7,598,389 B2 * | 10/2009 | Dunkel et al. | 548/110 |
| 7,767,623 B2 * | 8/2010 | Ehrenfreund et al. | 504/105 |
| 2001/0031890 A1 | 10/2001 | Riemneier | |
| 2007/0191454 A1 | 8/2007 | Dunkel et al. | |
| 2008/0064874 A1 | 3/2008 | Dunkel et al. | |

FOREIGN PATENT DOCUMENTS

| | | |
|---|---|---|
| GB | 886048 | 1/1962 |
| JP | 09144719 | 6/1997 |
| WO | 0149664 | 7/2001 |

OTHER PUBLICATIONS

Falcou, Aurelie et al. (DN 132:222898, CAPLUS, abstract of Tetrahederon (1999), 56(2), pp. 225-231).*  
Harmata, Michael et al. (DN 121:8769, abstract of Synthesis (1994), (2), 142-4.*  
Bartoli et al. (DN 109:230711, CAPLUS, abstract of Journal of the Chemical Society, Chemical Communications (1988), (12), 807-8).*  
Harmata, et al., A General, Regioselective Synthesis of 2-Alkylanilines, Synthesis, 1994, 142-144.  
Patent Abstracts of Japan, vol. 1997, No. 10, Oct. 31, 1997 & JP 09 144719 (OCHIAI:KK), Jun. 3, 1997.

Dorwald, F.A.; "Side Reactions in Organic Synthesis", 2005, Wiley: Weinheim p. IX of Preface.  
Arcadi, A., S. Cacchi and F. Marinelli (1986). "Palladium-catalysed reductive addition of aryl iodides to aryl and alkylethynylsilanes: A stereo and regioselective route to functionalized 2,2-disubstituted vinylsilanes." Tetrahedron Letters 27(52):6397-6400.  
Chatani, N., N. Amishiro, T. Morii, T. Yamashita and S. Murai (1995). "Pd-Catalyzed Coupling Reaction of Acetylenes, Iodotrimethylsilane, and Organozinc Reagents for the Stereoselective Synthesis of Vinylsilanes." Journal of Organic Chemistry 60(6):1834-1840.  
Chernyshev, E.A., M.E. Dolgaya and A.D. Petrov (1960). "[Nitration of aromatic sila-hydrocarbons in which the aromatic ring occupies various positions with respect to the silicon atom]." Izvestija Akademii Nauk, Otdelenie Chimiceskich Nauk 1960(8):1424-1428.

(Continued)

*Primary Examiner* — Sabiha Qazi  
(74) *Attorney, Agent, or Firm* — R. Kody Jones

(57) ABSTRACT

A fungicidal compound of formula (I):

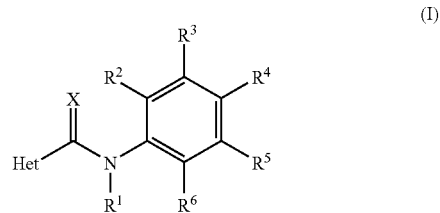

where Het is a 5- or 6-membered heterocyclic ring containing one to three heteroatoms, each independently selected from oxygen, nitrogen and sulphur, the ring being substituted by groups $R^7$, $R^8$ and $R^9$; $R^1$ is hydrogen, optionally substituted $(C_{1-4}$alkyl, optionally substituted $(C_{1-4}$alkylC(=O), optionally substituted $(C_{1-4}$alkylC(=O)O, optionally substituted $(C_{1-4})$alkoxy$(C_{1-4})$alkyl, optionally substituted allyl, optionally substituted propargyl or optionally substituted allenyl; $R^2$, $R^3$, $R^4$ and $R^5$ are each, independently, hydrogen, halogen, optionally substituted $(C_{1-4})$alkyl, optionally substituted $(C_{1-4})$alkoxy or optionally substituted $(C_{1-4})$alkoxy$(C_{1-4}$alkyl; $R^6$ is an organic group containing three to thirteen carbon atoms and at least one silicon atom and, optionally, one to three heteroatoms, each independently selected from oxygen, nitrogen and sulphur, and is optionally substituted by one to four independently selected halogen atoms; $R^7$, $R^8$ and $R^9$ are each, independently, hydrogen, halogen, $C_{1-3}$ alkyl, $C_{1-3}$ haloalkyl, $C_{1-3}$alkoxy$(C_{1-3})$alkyl or cyano, where at least one of $R^7$, $R^8$ and $R^9$ is not hydrogen; and X is O or S; or an N-oxide thereof; and when present, each optional substituent on alkyl moieties, allyl, propargyl and allenyl is, independently, selected from halogen, hydroxy, cyano, methoxycarbonyl, ethoxycarbonyl, methoxy, ethoxy, methylsulfonyl, ethylsulfonyl, difluoromethoxy, trifluoromethoxy and trifluorothiomethoxy.

8 Claims, No Drawings

OTHER PUBLICATIONS

Falcou, A., D. Marsacq, P. Hourquebie and A. Duchêne (2000). "General Access to ortho- and meta-Alkylanilines for the Synthesis of Polyanilines and Poly(Anilines-co-Substituted Anilines)." Tetrahedron 56(2):225-231.

Greene, T.W. and P.G.M. Wuts (2002). Protection for the Amino Group. In: Protective Groups in Organic Synthesis. John Wiley & Sons, Inc.: 494-653 (pp. 503-614 referenced).

Huang, X. and S.L. Buchwald (2001). "New Ammonia Equivalents for the Pd-Catalyzed Amination of Aryl Halides." Org. Lett. 3(21):3417-3419.

Hudrlik, P.F., E.L.O. Agwaramgbo and A.M. Hudrlik (1989). "Concerning the mechanism of the Peterson olefination reaction." Journal of Organic Chemistry 54(23):5613-5618.

Jeffery, T. (1999). "Tetraalkylammonium salt-based catalyst systems for directing the arylation of vinyltrimethylsilane." Tetrahedron Letters 40(9):1673-1676.

Jeffery, T. (2000). "Tetraalkylammonium salt-based catalyst systems for directing Heck-type reactions. Arylation of allyltrimethylsilane." Tetrahedron Letters 41(44):8445-8449.

Kang, K.-T., S. Sin Kim and J. Chul Lee (1991). "Synthesis of functionalized allylsilanes via palladium-catalyzed cross-coupling of 2-stannyl-3-silylpropene with organic halides." Tetrahedron Letters 32(34):4341-4344.

Kang, K.-T. and J. Sun U (1994). "Synthesis of $\beta$-Trimethylsilyl-$\beta$, $\gamma$-unsaturated Ketones via Lewis Acid Promoted Reactions of 2,3-bis(Trimethylsilyl)-propene with Acid Chlorides." Synthetic Communications 24(11):1507-1512.

Karabelas, K. and A. Hallberg (1986). "Synthesis of (E)-(2-arylethenyl)silanes by palladium-catalyzed arylation of vinylsilanes in the presence of silver nitrate." Journal of Organic Chemistry 51(26):5286-5290.

Maas, G., T. Werle, M. Alt and D. Mayer (1993). "Polymeric dicarbonyl ruthenium(I) acetate—An efficient catalyst for alkene cyclopropanation with diazoacetates." Tetrahedron 49(4):881-888.

Murata, M., S. Watanabe and Y. Masuda (1999). "Synthesis of alkenylsilanes via palladium(0)-catalyzed silylation of alkenyl iodides with hydrosilane." Tetrahedron Letters 40(52):9255-9257.

Nicolaou, K.C., A.D. Piscopio, P. Bertinato, T.K. Chakraborty, N. Minowa and K. Koide (1995). "Total Synthesis of Rapamycin." Chemistry—A European Journal 1(5):318-333.

Olofsson, K., M. Larhed and A. Hallberg (1998). "Highly Regioselective Palladium-Catalyzed Internal Arylation of Allyltrimethylsilane with Aryl Triflates." Journal of Organic Chemistry 63(15):5076-5079.

Smith, M.B. (2001). Preparation of Amines (Chapter 7). In: Compendium of Organic Synthetic Methods. vol. 9. New York: John Wiley & Sons, Inc.: 117-139.

Stuedemann, T., M. Ibrahim-Ouali and P. Knochel (1998). "A nickel-catalyzed carbozincation of aryl-substituted alkynes." Tetrahedron 54(7):1299-1316.

Urata, H., H. Suzuki, Y. Moro-oka and T. Ikawa (1984). "Catalytic Conversion of Allylic Esters to Corresponding Allylic Silanes with Hexamethyldisilane and Palladium(0) or Rhodium(I) Complexes." Bulletin of the Chemical Society of Japan 57(2):607-608.

Harmata, M. et al., "A General, Regioselective Synthesis of 2-Alkylanilines", Department of Chemistry, Synthesis, revised 1993, pp. 142-144.

Chamberlain, A.R., et al., "Vinyllithium Reagents from Arenesulfonylhydrazones", J. Org. Chem., vol. 43, No. 1, pp. 147-154, 1978.

* cited by examiner

CHEMICAL COMPOUNDS

The present invention relates to novel phenyl amides, substituted in the 2-position of the phenyl ring by a silicon containing substituent, which have microbiocidal activity, in particular fungicidal activity. The invention also relates to the preparation of these compounds, to novel intermediates used in the preparation of these compounds, to agrochemical compositions which comprise at least one of the novel compounds as active ingredient, to the preparation of the compositions mentioned and to the use of the active ingredients or compositions in agriculture or horticulture for controlling or preventing infestation of plants by phytopathogenic microorganisms, preferably fungi.

Certain phenyl amides, substituted in the 2-position of the phenyl ring by a silicon containing substituent, are disclosed in U.S.2001/0031890A1.

One particular aniline derivative is disclosed in Synthesis 1994, 142.

The present invention provides a compound of formula (I)

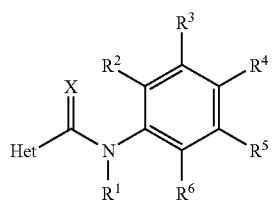

(I)

where Het is a 5- or 6-membered heterocyclic ring containing one to three heteroatoms, each independently selected from oxygen, nitrogen and sulphur, the ring being substituted by groups $R^7$, $R^8$ and $R^9$; $R^1$ is hydrogen, optionally substituted $(C_{1-4})$alkyl, optionally substituted $(C_{1-4})$alkylC(=O), optionally substituted $(C_{1-4})$alkylC(=O)O, optionally substituted $(C_{1-4})$alkoxy$(C_{1-4})$alkyl, optionally substituted allyl, optionally substituted propargyl or optionally substituted allenyl; $R^2$, $R^3$, $R^4$ and $R^5$ are each, independently, hydrogen, halogen, optionally substituted $(C_{1-4})$alkyl, optionally substituted $(C_{1-4})$alkoxy or optionally substituted $(C_{1-4})$alkoxy$(C_{1-4})$alkyl; $R^6$ is an organic group containing three to thirteen carbon atoms and at least one silicon atom and, optionally, one to three heteroatoms, each independently selected from oxygen, nitrogen and sulphur, and is optionally substituted by one to four independently selected halogen atoms; $R^7$, $R^8$ and $R^9$ are each, independently, hydrogen, halogen, $C_{1-3}$ alkyl, $C_{1-3}$haloalkyl, $C_{1-3}$alkoxy$(C_{1-3})$alkyl or cyano, where at least one of $R^7$, $R^8$ and $R^9$ is not hydrogen; and X is O or S; or an N-oxide thereof.

Halogen is fluorine, chlorine, bromine or iodine, preferably fluorine, chlorine or bromine.

Each alkyl moiety is a straight or branched chain and is, for example, methyl, ethyl, n-propyl, n-butyl, iso-propyl, n-butyl, sec-butyl, iso-butyl or tent-butyl.

The alkenyl moieties, where appropriate, can be of either the (E)- or (Z)-configuration.

When present, each optional substituent on alkyl moieties, allyl, propargyl and allenyl is, independently, selected from halogen, hydroxy, cyano, carboxyl, methoxycarbonyl, ethoxycarbonyl, methoxy, ethoxy, methylsulfonyl, ethylsulfonyl, difluoromethoxy, trifluoromethoxy and trifluorothiomethoxy; and more preferably is, independently, selected from halogen, hydroxy, cyano, methoxycarbonyl, ethoxycarbonyl, methoxy, ethoxy, methylsulfonyl, ethylsulfonyl, difluoromethoxy, trifluoromethoxy and trifluorothiomethoxy.

Preferably $R^1$ is hydrogen, propargyl, allenyl, $CH_3C(=O)$, $C_2H_5C(=O)$ or $CH_3OCH_2C(=O)$.

Most preferably $R^1$ is hydrogen.

Preferably $R^2$, $R^3$, $R^4$ and $R^5$ are each, independently, selected from hydrogen, halogen, methyl, trifluoromethyl and trifluoromethoxy.

More preferably $R^2$ is hydrogen.
More preferably $R^3$ is hydrogen.
More preferably $R^4$ is hydrogen.
More preferably $R^5$ is hydrogen.

It is preferred that Het is pyrazolyl, pyrrolyl, thiophenyl, furyl, thiazolyl, isothiazolyl, oxazolyl, isoxazolyl, triazolyl, pyridinyl, pyrazinyl, pyrimidinyl, pyridazinyl, 5,6-dihydropyrane or 5,6-dihydro-1,4-oxathiinyl (more preferably pyrazolyl, pyrrolyl, thiophenyl, furyl, thiazolyl, oxazolyl, pyridinyl, pyrimidinyl, pyridaziny, 5,6-dihydropyrane or 5,6-dihydro-1,4-oxathiinyl) each being substituted by groups $R^7$, $R^8$ and $R^9$.

Preferably $R^6$ is an aliphatic, saturated or unsaturated group containing three to thirteen carbon atoms and at least one silicon atom and, optionally, one to three heteroatoms, each independently selected from oxygen, nitrogen and sulphur, and is optionally substituted by one to four independently selected halogen atoms.

More preferably $R^6$ is $Y^1$—$Si(O_mMe)(O_nMe)(O_pY^2)$ where m, n and p are each, independently, 0 or 1; $Y^1$ is a bond or is alkandiyl (alkylene), alkendiyl (alkenylene), or alkindiyl (alkynylene), each of which is branched or unbranched and contains 1-6 carbon atoms optionally interrupted by one or two oxygen atoms and optionally substituted by up to three independently selected halogen atoms; and $Y^2$ is alkyl or alkenyl, each of which is branched or unbranched and contains 1-5 carbon atoms optionally interrupted by one heteroatom selected from O, S and N and optionally substituted by up to three independently selected halogen atoms.

Even more preferably $R^6$ is $SiMe_3$, $SiMe_2Et$, $SiMe_2CHMe_2$, $SiMe_2CH_2CHMe_2$, $SiMe_2CH_2CMe_3$, $SiMe_2OCHMe_2$, $SiMe_2OCH_2CHMe_2$, $CH_2SiMe_3$, $CH_2SiMe_2Et$, $CH_2SiMe_2CHMe_2$, $CH_2SiMe_2CH_2CHMe$, $CH_2SiMe_2OMe$, $CH_2SiMe_2OCHMe_2$, $CH_2SiMe_2OCH_2CHMe_2$, $CHMeSiMe_3$, $CHMeSiMe_2OMe$, $(CH_2)_2SiMe_3$, $(CH_2)_2SiMe_2Et$, $(CH_2)_2SiMe_2CHMe_2$, $(CH_2)_2SiMe_2CMe_3$, $(CH_2)_2SiMe_2CH_2CHMe_2$, $(CH_2)_2SiMe_2CH_2CH_2Me$, $(CH_2)_2SiMe_2CH_2CMe_3$, $(CH_2)_2SiMe_2OCHMe_2$, $(CH_2)_2SiMe_2OCH_2CHMe_2$, $CHMeCH_2SiMe_3$, $CHMeCH_2SiMe_2Et$, $CHMeCH_2SiMe_2CH_2CH_2Me$, $CHMeCH_2SiMe_2CHMe_2$, $CHMeCH_2SiMe_2CMe_3$, $CHMeCH_2SiMe_2CH_2CHMe_2$, $CFMeCH_2SiMe_3$, $CHMeCH_2CH_2SiMe_2OMe$, $CHMeCH_2SiMe_2OCHMe_2$, $CHMeCH_2SiMe_2OCH_2CHMe_2$, $CH_2CHMeSiMe_3$, $CH_2CHMeSiMe_2Et$, $CH_2CHMeSiMe_2CHMe_2$, $CHMeCH-MeSiMe_3$, $CMe_2CH_2SiMe_3$, $(CH_2)_3SiMe_3$, $(CH_2)_3SiMe_2Et$, $(CH_2)_3SiMe_2CHMe_2$, $(CH_2)_3SiMe_2CH_2CHMe_2$, $(CH_2)_3SiMe_2OMe$, $(CH_2)_3SiMe_2OCHMe_2$, $(CH_2)_3SiMe_2OCH_2CHMe_2$, $CHMeCH_2CH_2SiMe_3$, $CHMeCH_2CH_2SiMe_2Et$, $CHMeCH_2CH_2SiMe_2CHMe_2$, $CHMeCH_2CH_2CH_2SiMe_2OMe$, $CHMeCH_2CH_2SiMe_2OCHMe_2$, $CMe=CHSiMe_3$ or $CH_2CH_2SiMe_2OMe$.

Preferably $R^7$, $R^8$ and $R^9$ are each, independently, hydrogen, halogen, methyl, $CF_3$, $CF_2H$, $CH_2F$, $CF_2Cl$ or $CH_2OCH_3$ (where at least one of $R^7$, $R^8$ and $R^9$ is not hydrogen).

Preferably X is oxygen.

When a compound of formula (I) is an N-oxide then it is preferred that Het is pyridinyl substituted by groups $R^7$, $R^8$ and $R^9$.

Throughout this description, Me is used to represent the methyl group. Likewise, Et represents the ethyl group.

Anilines of formula (II):

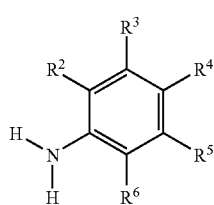

where $R^2$, $R^3$, $R^4$, $R^5$ and $R^6$ are as defined above for a compound of formula (I), are useful as intermediates in the preparation of compounds of formula (I).

Certain anilines of formula (II) are novel compounds, though one particular aniline is disclosed in Synthesis 1994, 142. Therefore, in another aspect the present invention provides a compound of formula (II) where $R^2$, $R^3$, $R^4$ and $R^5$ are each, independently, hydrogen, halogen, $CH_3$, $CF_3$ or $OCF_3$; $R^6$ is $(CHR^{10})(CH^{11}R^{12})_rSi(R^{13})(R^{14})(R^{15})$; r is 0, 1, 2 or 3; $R^{10}$ is $C_{1-3}$ alkyl or $C_{1-3}$ haloalkyl; and when r is 2 or 3 or when at least one of the $R^{11}$ and $R^{12}$ moieties is not hydrogen, then $R^{10}$ may also be hydrogen; each $R^{11}$ and each $R^{12}$ is, independently, chosen from hydrogen, halogen, $C_{1-3}$ alkyl and $C_{1-3}$ haloalkyl; or $R^{10}$ and $R^{11}$ on adjacent carbon atoms or two $R^{11}$ moieties on adjacent carbon atoms may together be a double bond; $R^{13}$ and $R^{14}$ are, independently, methyl or ethyl; and $R^{15}$ is $C_{1-6}$ alkyl, $C_{1-4}$ alkoxy$(C_{1-4})$alkyl, $C_{1-3}$ haloalkyl, $C_{2-6}$ alkenyl or $C_{1-6}$ alkoxy; provided that $R^6$ is such that its total number of carbon atoms is 5-13, its total number of halogen atoms is 0-4 and its total number of heteroatoms is 0-3; and provided that when $R^{10}$, $R^{13}$, $R^{14}$ and $R^{15}$ are each $CH_3$ and r is 0, then $R^2$, $R^3$, $R^4$ and $R^5$ are not all hydrogen.

Preferably $R^{10}$ is hydrogen or methyl.
Preferably $R^{11}$ is hydrogen or methyl.
Preferably $R^{12}$ is hydrogen or methyl.
Preferably $R^{13}$ is methyl.
Preferably $R^{14}$ is methyl.
Preferably $R^{15}$ is Me, Et, $CHMe_2$, $CH_2CH_2Me$, $CH_2CHMe_2$, OMe, $OCHMe_2$ or $OCH_2CHMe_2$.

For a compound of formula (II), preferably $R^6$ is $CHMeSiMe_3$, $CHMeSiMe_2OMe$, $(CH_2)_2SiMe_2OCH_2CHMe_2$, $CHMeCH_2SiMe_3$, $CHMeCH_2SiMe_2Et$, $CHMeCH_2SiMe_2CHMe_2$, $CHMeCH_2SiMe_2CMe_3$, $CHMeCH_2SiMe_2CH_2CHMe_2$, $CFMeCH_2SiMe_3$, $CHMeCH_2CH_2SiMe_2OMe$, $CHMeCH_2SiMe_2OCHMe_2$, $CHMeCH_2SiMe_2OCH_2CHMe_2$, $(CH_2)_3SiMe_3$, $(CH_2)_3SiMe_2Et$, $(CH_2)_3SiMe_2CHMe_2$, $(CH_2)_3SiMe_2CH_2CHMe_2$, $(CH_2)_3SiMe_2OMe$, $(CH_2)_3SiMe_2OCHMe_2$, $(CH_2)_3SiMe_2OCH_2CHMe_2$, $CHMeCH_2CH_2SiMe_3$, $CHMeCH_2CH_2SiMe_2Et$, $CHMeCH_2CH_2SiMe_2CHMe_2$, $CHMeCH_2CH_2CH_2SiMe_2OMe$, $CHMeCH_2CH_2SiMe_2OCHMe_2$, $CH_2CHMeSiMe_3$, $CH_2CMe_2SiMe_3$, $CH_2CHMeSiMe_2Et$ or $(CHMe)_2SiMe_3$.

The compounds of formula (I) and of formula (II) may exist as different geometric or optical isomers or in different tautomeric forms. This invention covers all such isomers and tautomers and mixtures thereof in all proportions as well as isotopic forms such as deuterated compounds.

The compounds in Tables 1 to 16 below illustrate particularly preferred compounds of the invention.

Table A represents Table 1 (when A is 1) and represents Table 2 (when A is 2).

TABLE A

| Compound No. | $R^1$ | $R^6$ | $R^7$ | $R^8$ | $R^9$ | X |
|---|---|---|---|---|---|---|
| A.1 | H | $SiMe_3$ | H | Me | $CF_3$ | O |
| A.2 | H | $SiMe_3$ | H | Me | $CF_2H$ | O |
| A.3 | H | $CH_2SiMe_3$ | H | Me | $CF_3$ | O |
| A.4 | H | $CH_2SiMe_3$ | H | Me | $CF_3$ | S |
| A.5 | H | $CH_2SiMe_3$ | H | Me | $CF_2H$ | O |
| A.6 | propargyl | $CH_2SiMe_3$ | H | Me | $CF_3$ | O |
| A.7 | H | $CHMeSiMe_3$ | H | Me | $CF_3$ | O |
| A.8 | H | $CHMeSiMe_3$ | H | Me | $CF_2H$ | O |
| A.9 | H | $CHMeSiMe_3$ | H | Me | $CF_3$ | S |
| A.10 | propargyl | $CHMeSiMe_3$ | H | Me | $CF_3$ | O |
| A.11 | allenyl | $CHMeSiMe_3$ | H | Me | $CF_3$ | O |
| A.12 | COMe | $CHMeSiMe_3$ | H | Me | $CF_3$ | O |
| A.13 | H | $CHMeSiMe_3$ | F | Me | Me | O |
| A.14 | H | $(CH_2)_2SiMe_3$ | H | Me | $CF_3$ | O |
| A.15 | H | $(CH_2)_2SiMe_3$ | H | Me | $CF_3$ | S |
| A.16 | H | $(CH_2)_2SiMe_3$ | H | Me | $CF_2H$ | O |
| A.17 | propargyl | $(CH_2)_2SiMe_3$ | H | Me | $CF_3$ | O |
| A.18 | H | $(CH_2)_2SiMe_3$ | F | Me | Me | O |
| A.19 | H | $(CH_2)_2SiMe_3$ | H | $CH_2OMe$ | $CF_3$ | O |
| A.20 | H | $(CH_2)_2SiMe_3$ | H | $CH_2OMe$ | $CF_2H$ | O |
| A.21 | H | $CHMeCH_2SiMe_3$ | H | Me | $CF_3$ | O |
| A.22 | H | $CHMeCH_2SiMe_3$ | H | Me | $CF_3$ | S |
| A.23 | H | $CHMeCH_2SiMe_3$ | H | $CH_2OMe$ | $CF_3$ | O |
| A.24 | H | $CHMeCH_2SiMe_3$ | H | Me | $CF_2H$ | O |
| A.25 | H | $CHMeCH_2SiMe_3$ | H | Me | $CF_2H$ | S |
| A.26 | propargyl | $CHMeCH_2SiMe_3$ | H | Me | $CF_3$ | O |
| A.27 | allenyl | $CHMeCH_2SiMe_3$ | H | Me | $CF_3$ | O |
| A.28 | propargyl | $CHMeCH_2SiMe_3$ | H | Me | $CF_2H$ | O |
| A.29 | allenyl | $CHMeCH_2SiMe_3$ | H | Me | $CF_2H$ | O |

TABLE A-continued

| Compound No. | R¹ | R⁶ | R⁷ | R⁸ | R⁹ | X |
|---|---|---|---|---|---|---|
| A.30 | H | CHMeCH₂SiMe₃ | F | Me | Me | O |
| A.31 | COMe | CHMeCH₂SiMe₃ | H | Me | CF₃ | O |
| A.32 | H | (CH₂)₃SiMe₃ | H | Me | CF₂H | O |
| A.33 | H | CH₂Si(Me₂)Et | H | Me | CF₃ | O |
| A.34 | H | CH₂Si(Me₂)Et | H | Me | CF₂H | O |
| A.35 | H | CH₂Si(Me₂)CHMe₂ | H | Me | CF₃ | O |
| A.36 | H | CH₂Si(Me₂)CHMe₂ | H | Me | CF₂H | O |
| A.37 | H | CH₂Si(Me₂)OMe | H | Me | CF₃ | O |
| A.38 | H | CH₂Si(Me₂)OMe | H | Me | CF₂H | O |
| A.39 | H | CH₂CH₂Si(Me₂)OMe | H | Me | CF₃ | O |
| A.40 | H | CHMeSi(Me₂)OMe | H | Me | CF₃ | O |
| A.41 | H | CHMeSi(Me₂)OMe | H | Me | CF₂H | O |
| A.42 | H | CH₂CH₂Si(Me₂)OMe | H | Me | CF₂H | O |
| A.43 | H | C(Me)=CHSiMe₃ | H | Me | CF₃ | O |
| A.44 | H | SiMe₃ | H | Me | CH₂F | O |
| A.45 | H | (CH₂)₂SiMe₃ | H | Me | CH₂F | O |
| A.46 | H | CH₂CHMeSiMe₃ | H | Me | CH₂F | O |
| A.47 | H | CH₂CHMeSiMe₃ | H | Me | CF₃ | O |
| A.48 | H | CH₂CHMeSiMe₃ | H | Me | CF₂H | O |
| A.49 | H | CHMeCH₂SiMe₃ | H | Me | CH₂F | O |
| A.50 | H | CMe₂CH₂SiMe₃ | H | Me | CF₃ | O |
| A.51 | H | CMe₂CH₂SiMe₃ | H | Me | CF₂H | O |
| A.52 | H | CHMeCHMeSiMe₃ | H | Me | CF₂H | O |
| A.53 | H | CHMeCHMeSiMe₃ | H | Me | CF₃ | O |
| A.54 | H | CH₂CMe₂SiMe₃ | H | Me | CF₃ | O |
| A.55 | H | CH₂CMe₂SiMe₃ | H | Me | CF₂H | O |
| A.56 | H | CHMe(CH₂)₂SiMe₃ | H | Me | CF₂H | O |
| A.57 | H | CHMe(CH₂)₂SiMe₃ | H | Me | CF₃ | O |
| A.58 | H | (CH₂)₂Si(Me₂)(CH₂)₂Me | H | Me | CF₂H | O |
| A.59 | H | (CH₂)₂Si(Me₂)(CH₂)₂Me | H | Me | CF₃ | O |
| A.60 | H | CHMeCH₂Si(Me₂)CMe₃ | H | Me | CF₃ | O |
| A.61 | H | C(=CH₂)CH₂Si(Me₂)CMe₃ | H | Me | CF₃ | O |
| A.62 | H | C(=CH₂)CH₂Si(Me₂)CH₂Me | H | Me | CF₃ | O |
| A.63 | H | (CH₂)₂Si(Me₂)CH₂Me | H | Me | CF₃ | O |
| A.64 | H | CHMeCH₂Si(Me₂)CH₂Me | H | Me | CF₃ | O |
| A.65 | H | (CH₂)₂Si(Me₂)CHMe₂ | H | Me | CF₃ | O |
| A.66 | H | CHMeCH₂Si(Me₂)CHMe₂ | H | Me | CF₃ | O |
| A.67 | H | CHMeCH₂Si(Me₂)CH₂CHMe₂ | H | Me | CF₃ | O |
| A.68 | H | Si(Me₂)CH₂Me | H | Me | CF₂H | O |
| A.69 | H | Si(Me₂)CH₂Me | H | Me | CF₃ | O |
| A.70 | H | Si(Me₂)CHMe₂ | H | Me | CF₃ | O |
| A.71 | H | Si(Me₂)CHMe₂ | H | Me | CF₂H | O |
| A.72 | H | Si(Me₂)CH₂CHMe₂ | H | Me | CF₂H | O |
| A.73 | H | Si(Me₂)CH₂CHMe₂ | H | Me | CF₃ | O |
| A.74 | H | C:CCH₂SiMe₃ | H | Me | CF₃ | O |
| A.75 | propargyl | (CH₂)₂SiMe₃ | H | Me | CF₂H | O |
| A.76 | allenyl | (CH₂)₂SiMe₃ | H | Me | CF₂H | O |
| A.77 | allenyl | (CH₂)₂SiMe₃ | H | Me | CF₃ | O |
| A.78 | H | (CH₂)₂SiMe₃ | H | Me | CF₂Cl | O |
| A.79 | H | (CH₂)₃SiMe₃ | H | Me | CF₃ | O |
| A.80 | H | (CH₂)₂SiMe₃ | Br | Me | CF₃ | O |
| A.81 | H | (CH₂)₂SiMe₃ | Cl | Me | CF₃ | O |
| A.82 | H | (CH₂)₂SiMe₃ | H | Me | Me | O |

Table 1 provides 82 compounds of formula (Ia) where $R^1$, $R^6$, $R^7$, $R^8$, $R^9$ and X are as defined in Table 1.

Table 2 provides 82 compounds of formula (Ib) where $R^1$, $R^6$, $R^7$, $R^8$, $R^9$ and X are as defined in Table 2.

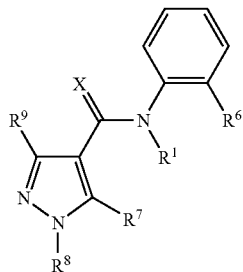

(Ia)

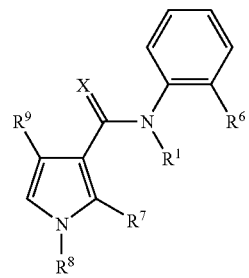

(Ib)

Table B represents Table 3 (when B is 3) and represents Table 4 (when B is 4).

TABLE B

| Compound No. | $R^1$ | $R^6$ | $R^8$ | $R^9$ | X |
|---|---|---|---|---|---|
| B.1 | H | SiMe₃ | Me | CF₃ | O |
| B.2 | H | SiMe₃ | Me | CF₂H | O |
| B.3 | H | CH₂SiMe₃ | Me | CF₃ | O |
| B.4 | H | CH₂SiMe₃ | Me | CF₃ | S |
| B.5 | H | CH₂SiMe₃ | Me | CF₂H | O |
| B.6 | propargyl | CH₂SiMe₃ | Me | CF₃ | O |
| B.7 | H | CHMeSiMe₃ | Me | CF₃ | O |
| B.8 | H | CHMeSiMe₃ | Me | CF₂H | O |
| B.9 | H | CHMeSiMe₃ | Me | CF₃ | S |
| B.10 | propargyl | CHMeSiMe₃ | Me | CF₃ | O |
| B.11 | allenyl | CHMeSiMe₃ | Me | CF₃ | O |
| B.12 | COMe | CHMeSiMe₃ | Me | CF₃ | O |
| B.13 | H | CHMeSiMe₃ | Me | Me | O |
| B.14 | H | (CH₂)₂SiMe₃ | Me | CF₃ | O |
| B.15 | H | (CH₂)₂SiMe₃ | Me | CF₃ | S |
| B.16 | H | (CH₂)₂SiMe₃ | Me | CF₂H | O |
| B.17 | propargyl | (CH₂)₂SiMe₃ | Me | CF₃ | O |
| B.18 | H | (CH₂)₂SiMe₃ | Me | Me | O |
| B.19 | H | (CH₂)₂SiMe₃ | CF₃ | CF₃ | O |
| B.20 | H | CHMeCH₂SiMe₃ | Me | CF₃ | O |
| B.21 | H | CHMeCH₂SiMe₃ | Me | CF₃ | S |
| B.22 | H | CHMeCH₂SiMe₃ | Me | CF₂H | O |
| B.23 | H | CHMeCH₂SiMe₃ | Me | CF₂H | S |
| B.24 | propargyl | CHMeCH₂SiMe₃ | Me | CF₃ | O |
| B.25 | propargyl | CHMeCH₂SiMe₃ | Me | CF₂H | O |
| B.26 | H | CHMeCH₂SiMe₃ | Me | Me | O |
| B.27 | H | CHMeCH₂SiMe₃ | CF₃ | CF₃ | O |
| B.28 | COMe | CHMeCH₂SiMe₃ | Me | CF₃ | O |
| B.29 | H | (CH₂)₃SiMe₃ | Me | CF₃ | O |
| B.30 | H | (CH₂)₃SiMe₃ | Me | CF₂H | O |
| B.31 | H | CH₂Si(Me₂)Et | Me | CF₃ | O |
| B.32 | H | CH₂Si(Me₂)Et | Me | CF₂H | O |
| B.33 | H | CH₂Si(Me₂)CHMe₂ | Me | CF₃ | O |
| B.34 | H | CH₂Si(Me₂)CHMe₂ | Me | CF₂H | O |
| B.35 | H | CH₂CHMeSiMe₃ | Me | CF₃ | O |
| B.36 | H | CH₂CHMeSiMe₃ | Me | CF₂H | O |
| B.37 | H | CMe₂CH₂SiMe₃ | Me | CF₃ | O |
| B.38 | H | CMe₂CH₂SiMe₃ | Me | CF₂H | O |
| B.39 | H | CHMeCHMeSiMe₃ | Me | CF₂H | O |
| B.40 | H | CHMeCHMeSiMe₃ | Me | CF₃ | O |
| B.41 | H | CH₂CMe₂SiMe₃ | Me | CF₃ | O |
| B.42 | H | CH₂CMe₂SiMe₃ | Me | CF₂H | O |
| B.43 | H | CHMe(CH₂)₂SiMe₃ | Me | CF₂H | O |
| B.44 | H | CHMe(CH₂)₂SiMe₃ | Me | CF₃ | O |
| B.45 | H | (CH₂)₂SiMe₃ | CH₂OMe | CH₂Me | O |
| B.46 | H | (CH₂)₂SiMe₃ | CH₂OCH₂Me | CH₂Me | O |

Table 3 provides 46 compounds of formula (Ic) where $R^1$, $R^6$, $R^8$, $R^9$ and X are as defined in Table 3.

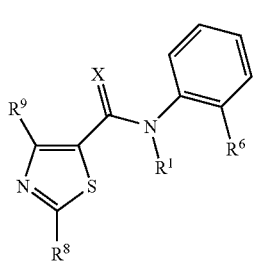

(Ic)

Table 4 provides 46 compounds of formula (Id) where $R^1$, $R^6$, $R^8$, $R^9$ and X are as defined in Table 4.

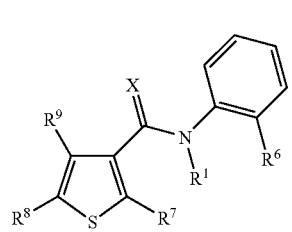

(Id)

Table C represents Table 5 (when V is 5) and represents Table 6 (when C is 6).

TABLE C

| Compound No. | $R^1$ | $R^6$ | $R^7$ | $R^8$ | $R^9$ | X |
|---|---|---|---|---|---|---|
| C.1 | H | SiMe₃ | Me | Me | H | O |
| C.2 | H | SiMe₃ | Me | Me | H | O |
| C.3 | H | CH₂SiMe₃ | Me | Me | Me | O |
| C.4 | H | CH₂SiMe₃ | Me | Me | CF₃ | O |
| C.5 | H | CH₂SiMe₃ | Me | Me | H | O |
| C.6 | propargyl | CH₂SiMe₃ | Me | Me | CF₃ | O |
| C.7 | H | CHMeSiMe₃ | Me | Me | CF₃ | O |
| C.8 | H | CHMeSiMe₃ | Me | Me | Me | O |
| C.9 | H | CHMeSiMe₃ | Me | Me | Me | S |
| C.10 | propargyl | CHMeSiMe₃ | Me | Me | Me | O |
| C.11 | allenyl | CHMeSiMe₃ | Me | Me | Me | O |
| C.12 | COMe | CHMeSiMe₃ | Me | Me | Me | O |
| C.13 | H | CHMeSiMe₃ | Me | Me | Me | O |
| C.14 | H | (CH₂)₂SiMe₃ | Me | Me | CF₃ | O |
| C.15 | H | (CH₂)₂SiMe₃ | H | H | CF₃ | O |
| C.16 | H | (CH₂)₂SiMe₃ | H | H | CF₃ | S |
| C.17 | propargyl | (CH₂)₂SiMe₃ | H | H | CF₃ | O |
| C.18 | H | (CH₂)₂SiMe₃ | Me | Me | H | O |
| C.19 | H | CHMeCH₂SiMe₃ | H | H | CF₃ | O |
| C.20 | H | CHMeCH₂SiMe₃ | H | H | CF₃ | S |
| C.21 | H | CHMeCH₂SiMe₃ | Me | Me | Me | O |
| C.22 | H | CHMeCH₂SiMe₃ | H | Me | CF₃ | O |
| C.23 | H | CHMeCH₂SiMe₃ | Me | Me | H | O |
| C.24 | COMe | CHMeCH₂SiMe₃ | Me | Me | H | O |
| C.25 | propargyl | CHMeCH₂SiMe₃ | Me | Me | H | O |
| C.26 | allenyl | CHMeCH₂SiMe₃ | Me | Me | H | O |
| C.27 | propargyl | CHMeCH₂SiMe₃ | Me | Me | Me | O |
| C.28 | allenyl | CHMeCH₂SiMe₃ | Me | Me | Me | O |
| C.29 | COMe | CHMeCH₂SiMe₃ | Me | Me | Me | O |
| C.30 | COEt | CHMeCH₂SiMe₃ | Me | Me | Me | O |
| C.31 | H | CH₂CHMeSiMe₃ | H | H | CF₃ | O |
| C.32 | H | CH₂CHMeSiMe₃ | H | H | CF₃ | S |
| C.33 | H | CH₂CHMeSiMe₃ | Me | Me | Me | O |
| C.34 | H | CH₂CHMeSiMe₃ | H | Me | CF₃ | O |
| C.35 | H | CH₂CHMeSiMe₃ | Me | Me | H | O |

Table 5 provides 35 compounds of formula (Ie) where $R^1$, $R^6$, $R^7$, $R^8$, $R^9$ and X are as defined in Table 5.

(Ie)

Table 6 provides 35 compounds of formula (If) where $R^1$, $R^6$, $R^7$, $R^8$, $R^9$ and X are as defined in Table 6.

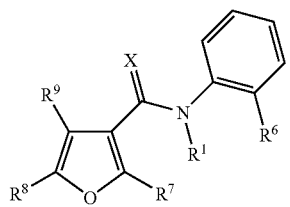

(If)

Table D represents Table 7 (when D is 7) and represents Table 8 (when D is 8).

TABLE D

| Compound No. | $R^1$ | $R^6$ | $R^7$ | X |
|---|---|---|---|---|
| D.1 | H | SiMe$_3$ | Me | O |
| D.2 | H | SiMe$_3$ | CF$_3$ | O |
| D.3 | H | CH$_2$SiMe$_3$ | Me | O |
| D.4 | H | CH$_2$SiMe$_3$ | CF$_3$ | S |
| D.5 | COMe | CH$_2$SiMe$_3$ | Me | O |
| D.6 | propargyl | CH$_2$SiMe$_3$ | Me | O |
| D.7 | H | CHMeSiMe$_3$ | Me | O |
| D.8 | H | CHMeSiMe$_3$ | CF$_3$ | O |
| D.9 | H | CHMeSiMe$_3$ | CF$_3$ | S |
| D.10 | propargyl | CHMeSiMe$_3$ | Me | O |
| D.11 | allenyl | CHMeSiMe$_3$ | Me | O |
| D.12 | COMe | CHMeSiMe$_3$ | Me | O |
| D.13 | propargyl | CHMeSiMe$_3$ | CF$_3$ | O |
| D.14 | H | (CH$_2$)$_2$SiMe$_3$ | Me | O |
| D.15 | H | (CH$_2$)$_2$SiMe$_3$ | CF$_3$ | O |
| D.16 | H | (CH$_2$)$_2$SiMe$_3$ | CF$_3$ | S |
| D.17 | propargyl | (CH$_2$)$_2$SiMe$_3$ | Me | O |
| D.18 | COMe | (CH$_2$)$_2$SiMe$_3$ | Me | O |
| D.19 | H | CHMeCH$_2$SiMe$_3$ | Me | O |
| D.20 | H | CHMeCH$_2$SiMe$_3$ | CF$_3$ | O |
| D.21 | H | CHMeCH$_2$SiMe$_3$ | CF$_3$ | S |
| D.22 | propargyl | CHMeCH$_2$SiMe$_3$ | Me | O |
| D.23 | allenyl | CHMeCH$_2$SiMe$_3$ | Me | O |
| D.24 | COMe | CHMeCH$_2$SiMe$_3$ | Me | O |
| D.25 | propargyl | CHMeCH$_2$SiMe$_3$ | CF$_3$ | O |
| D.26 | allenyl | CHMeCH$_2$SiMe$_3$ | CF$_3$ | O |
| D.27 | COMe | CHMeCH$_2$SiMe$_3$ | CF$_3$ | O |
| D.28 | allenyl | CHMeCH$_2$SiMe$_3$ | Me | O |
| D.29 | H | (CH$_2$)$_3$SiMe$_3$ | Me | O |
| D.30 | H | (CH$_2$)$_3$SiMe$_3$ | CF$_3$ | O |
| D.31 | H | CH$_2$CHMeSiMe$_3$ | Me | O |
| D.32 | H | CH$_2$CHMeSiMe$_3$ | CF$_3$ | O |

Table 7 provides 32 compounds of formula (Ig) where $R^1$, $R^6$, $R^7$ and X are as defined in Table 7.

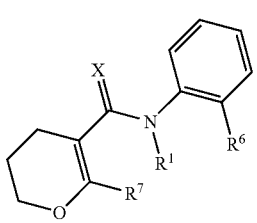

(Ig)

Table 8 provides 32 compounds of formula (Ih) where $R^1$, $R^6$, $R^7$ and X are as defined in Table 8.

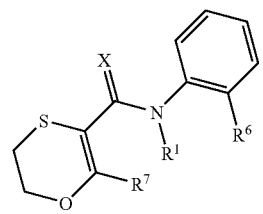

(Ih)

Table E represents Table 9 (when E is 9), represents Table 10 (when E is 10) and represents Table 11 (when E is 11).

TABLE E

| Compound No. | $R^1$ | $R^6$ | $R^7$ | X |
|---|---|---|---|---|
| E.1 | H | SiMe$_3$ | Cl | O |
| E.2 | H | SiMe$_3$ | CF$_3$ | O |
| E.3 | H | CH$_2$SiMe$_3$ | Cl | O |
| E.4 | H | CH$_2$SiMe$_3$ | Br | O |
| E.5 | H | CH$_2$SiMe$_3$ | CF$_3$ | O |
| E.6 | propargyl | CH$_2$SiMe$_3$ | Cl | O |
| E.7 | H | CHMeSiMe$_3$ | Cl | O |
| E.8 | H | CHMeSiMe$_3$ | Br | O |
| E.9 | H | CHMeSiMe$_3$ | CF$_3$ | O |
| E.10 | propargyl | CHMeSiMe$_3$ | Cl | O |
| E.11 | allenyl | CHMeSiMe$_3$ | Cl | O |
| E.12 | COMe | CHMeSiMe$_3$ | Cl | O |
| E.13 | H | CHMeSiMe$_3$ | Cl | S |
| E.14 | H | (CH$_2$)$_2$SiMe$_3$ | Cl | O |
| E.15 | H | (CH$_2$)$_2$SiMe$_3$ | Br | O |
| E.16 | H | (CH$_2$)$_2$SiMe$_3$ | CF$_3$ | O |
| E.17 | propargyl | (CH$_2$)$_2$SiMe$_3$ | Cl | O |
| E.18 | COMe | (CH$_2$)$_2$SiMe$_3$ | Cl | O |
| E.19 | H | CHMeCH$_2$SiMe$_3$ | Cl | O |
| E.20 | H | CHMeCH$_2$SiMe$_3$ | Cl | S |
| E.21 | H | CHMeCH$_2$SiMe$_3$ | Br | O |
| E.22 | H | CHMeCH$_2$SiMe$_3$ | CF$_3$ | O |
| E.23 | propargyl | CHMeCH$_2$SiMe$_3$ | Cl | O |
| E.24 | allenyl | CHMeCH$_2$SiMe$_3$ | Cl | O |
| E.25 | COMe | CHMeCH$_2$SiMe$_3$ | Cl | O |
| E.26 | propargyl | CHMeCH$_2$SiMe$_3$ | Br | O |
| E.27 | allenyl | CHMeCH$_2$SiMe$_3$ | Br | O |
| E.28 | COMe | CHMeCH$_2$SiMe$_3$ | Br | O |
| E.29 | COCH$_2$OMe | CHMeCH$_2$SiMe$_3$ | Cl | O |
| E.30 | COCH$_2$OMe | CHMeCH$_2$SiMe$_3$ | CF$_3$ | O |
| E.31 | H | (CH$_2$)$_3$SiMe$_3$ | Cl | O |
| E.32 | H | (CH$_2$)$_3$SiMe$_3$ | Br | O |
| E.33 | H | (CH$_2$)$_3$SiMe$_3$ | CF$_3$ | O |
| E.34 | H | CH$_2$CHMeSiMe$_3$ | CF$_3$ | O |
| E.35 | H | CH$_2$CHMeSiMe$_3$ | Cl | O |
| E.36 | H | CH$_2$CHMeSiMe$_3$ | Br | O |
| E.37 | H | SiMe$_2$CH$_2$Me | CF$_3$ | O |
| E.38 | H | SiMe$_2$CH$_2$Me | Cl | O |
| E.39 | H | SiMe$_2$CH$_2$Me | Br | O |
| E.40 | H | SiMe$_2$CHMe$_2$ | CF$_3$ | O |
| E.41 | H | SiMe$_2$CHMe$_2$ | Cl | O |
| E.42 | H | SiMe$_2$CHMe$_2$ | Br | O |
| E.43 | H | SiMe$_2$CH$_2$CH$_2$Me | CF$_3$ | O |
| E.44 | H | SiMe$_2$CH$_2$CH$_2$Me | Cl | O |
| E.45 | H | SiMe$_2$CH$_2$CH$_2$Me | Br | O |

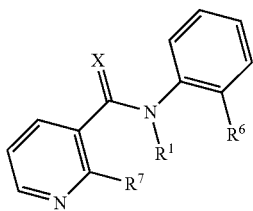

(Ii)

Table 9 provides 45 compounds of formula (Ii) where $R^1$, $R^6$, $R^7$ and X are as defined in Table 9.

Table 10 provides 45 compounds of formula (Ij) where $R^1$, $R^6$, $R^7$, $R^8$, $R^9$ and X are as defined in Table 10.

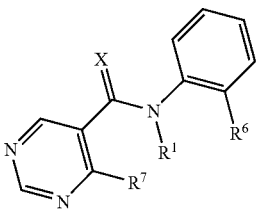

(Ij)

Table 11 provides 45 compounds of formula (Ik) where $R^1$, $R^6$, $R^7$, $R^8$, $R^9$ and X are as defined in Table 11.

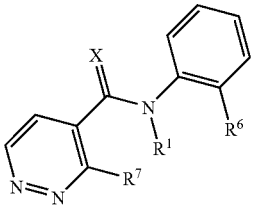

(Ik)

Table F represents Table 12 (when F is 12), Table 13 (when F is 13) and Table 14 (when F is 14).

TABLE F

| Compound Number | $R^1$ | $(R)_n$ |
|---|---|---|
| F.1 | $CF_3$ | 3-F |
| F.2 | $CF_3$ | 4-F |
| F.3 | $CF_3$ | 5-F |
| F.4 | $CF_3$ | 6-F |
| F.5 | $CF_3$ | 3-F,4-F |
| F.6 | $CF_3$ | 3-F,5-F |
| F.7 | $CF_3$ | 3-F,6-F |
| F.8 | $CF_2H$ | 3-F |
| F.9 | $CF_2H$ | 4-F |
| F.10 | $CF_2H$ | 5-F |
| F.11 | $CF_2H$ | 6-F |
| F.12 | $CF_2H$ | 3-F,4-F |
| F.13 | $CF_2H$ | 3-F,5-F |
| F.14 | $CF_2H$ | 3-F,6-F |

Table 12 provides 14 compounds of formula (Im) where $R^1$ and $(R)_n$ are as defined in Table 12.

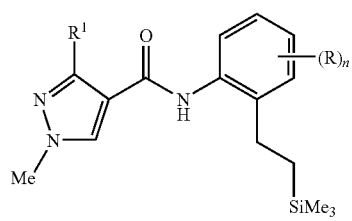

(Im)

Table 13 provides 14 compounds of formula (In) where $R^1$ and $(R)_n$ are as defined in Table 13.

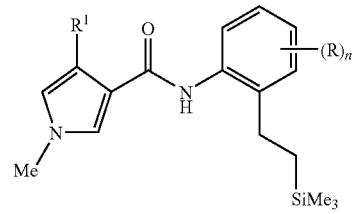

(In)

Table 14 provides 14 compounds of formula (Io) where $R^1$ and $(R)_n$ are as defined in Table 14.

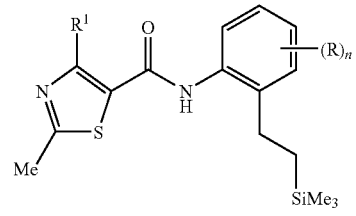

(Io)

Table 15 provides 9 compounds of formula (Ip) where $(R)_n$ is as defined in Table 15.

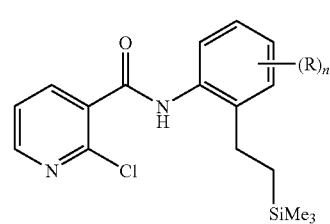

(Ip)

TABLE 15

| Compound Number | $(R)_n$ |
|---|---|
| 15.1 | 3-F |
| 15.2 | 4-F |
| 15.3 | 5-F |
| 15.4 | 6-F |
| 15.5 | 3-F,4-F |
| 15.6 | 3-F,5-F |
| 15.7 | 3-F,6-F |
| 15.8 | 4-F,5-F |
| 15.9 | 4-F,6-F |

Table 16 provides 27 compounds of formula (IIa) where $R^6$ is as defined in Table 16.

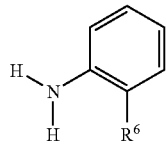
(IIa)

TABLE 16

| Compound Number | $R^6$ |
|---|---|
| 16.1 | $CHMeSiMe_2OMe$ |
| 16.2 | $(CH_2)_2SiMe_2OCH_2CHMe_2$ |
| 16.3 | $CHMeCH_2SiMe_3$ |
| 16.4 | $CHMeCH_2SiMe_2Et$ |
| 16.5 | $CHMeCH_2SiMe_2CHMe_2$ |
| 16.6 | $CHMeCH_2SiMe_2CMe_3$ |
| 16.7 | $CHMeCH_2SiMe_2CH_2CHMe_2$ |
| 16.8 | $CFMeCH_2SiMe_3$ |
| 16.9 | $CHMeCH_2CH_2SiMe_2OMe$ |
| 16.10 | $CHMeCH_2SiMe_2OCHMe_2$ |
| 16.11 | $CHMeCH_2SiMe_2OCH_2CHMe_2$ |
| 16.12 | $(CH_2)_3SiMe_3$ |
| 16.13 | $(CH_2)_3SiMe_2Et$ |
| 16.14 | $(CH_2)_3SiMe_2CHMe_2$ |
| 16.15 | $(CH_2)_3SiMe_2CH_2CHMe_2$ |
| 16.16 | $(CH_2)_3SiMe_2OMe$ |
| 16.17 | $(CH_2)_3SiMe_2OCHMe_2$ |
| 16.18 | $(CH_2)_3SiMe_2OCH_2CHMe_2$ |
| 16.19 | $CHMeCH_2CH_2SiMe_3$ |
| 16.20 | $CHMeCH_2CH_2SiMe_2Et$ |
| 16.21 | $CHMeCH_2CH_2SiMe_2CHMe_2$ |

TABLE 16-continued

| Compound Number | $R^6$ |
|---|---|
| 16.22 | $CHMeCH_2CH_2CH_2SiMe_2OMe$ |
| 16.23 | $CHMeCH_2CH_2SiMe_2OCHMe_2$ |
| 16.24 | $CH_2CHMeSiMe_3$ |
| 16.25 | $CH_2CHMeSiMe_2Et$ |
| 16.26 | $(CHMe)_2SiMe_3$ |
| 16.27 | $CH_2CMe_2SiMe_3$ |

Throughout this description, temperatures are given in degrees Celsius; "NMR" means nuclear magnetic resonance spectrum; MS stands for mass spectrum; and "%" is percent by weight, unless corresponding concentrations are indicated in other units.

The following abbreviations are used throughout this description:

| | |
|---|---|
| m.p. = melting point | b.p. = boiling point. |
| s = singlet | br = broad |
| d = doublet | dd = doublet of doublets |
| t = triplet | q = quartet |
| m = multiplet | ppm = parts per million |
| qd = quartet of doublets | sext = sextet |

Table 17 shows selected melting point selected NMR data, all with $CDCl_3$ as the solvent (unless otherwise stated; if a mixture of solvents is present, this is indicated as, for example, $(CDCl_3/d_6\text{-}DMSO)$) and characteristic mass spectrum signals (no attempt is made to list all characterising data in all cases) for compounds of Tables 1 to 16. A compound number which ends with the letter 'A' relates only to its (−) enantiomer and a compound number which ends with the letter 'B' relates only to its (+) enantiomer.

TABLE 17

| Compound Number | $^1$H-NMR data: (ppm/multiplicity/number of Hs) or mass spectrum signal | m.p./(° C.) |
|---|---|---|
| 1.1 | 0.0 (s, 9); 3.7 (s, 3); 7.0-7.5 (m, 5); 7.7 (s, br., 1) | 127-128 |
| 1.2 | | 148-149 |
| 1.3 | 0.0 (s, 9); 2.3 (s, 2); 4.05 (s, 3); 7.15 (m, 3); 7.35 (m, 1); 8.5 (s, 1). | 161-162 |
| 1.7 | −0.1 (s, 9); 1.3 (d, 3); 2.5 (q.1 coinciding with DMSO signal); 4.0 (s, 3); 7.1-7.35 (m, 4); 8.5 (s, 1); 9.5 (s, 1). | 187-188 |
| 1.14 | 0.0 (s, 9); 0.8 (m, 2); 2.6 (m, 2); 4.05 (s, 3); 7.2-7.4 (2m, 3, 1); 8.5 (s, 1); 9.7 (s, 1). | 122-124 |
| 1.16 | 0.0 (s, 9); 0.8 (m, 2); 2.6 (m, 2); 3.9 (s, 3); 6.8 (t, 1) 7.1-7.3 (m, 3), 7.7-8.1 (m, 3). | 109-111 |
| 1.17 | | 121-122 |
| 1.21 (racemic) | −0.1 (s, 9); 1.0 (q of d, 2); 1.2 (d, 3); 3.1 (sext.1); 3.95 (s, 3); 7.2 (m, 2); 7.4 (m, 1); 7.6 (br.s, 1); 7.7 (m, 1); 8.1 (s, 1). | 149-150 |
| 1.21A | | 95-98 |
| 1.21B | | 101-104 |
| 1.24 | −0.1 (s, 9); 1.0 (q of d, 2); 1.3 (d, 3); 3.2 (sext.1); 3.95 (s, 3); 6.9 (t, 3); 7.2 (m, 2); 7.4 (m, 1); 7.7 (m, 1); 8.0 (br.s, 1); 8.1 (s, 1). | 124-126 |
| 1.24A | | 77-79 |
| 1.24B | | 79-82 |
| 1.26 | | 126-128 |
| 1.27 | | 114-116 |
| 1.32 | | 85-87 |
| 1.43 | 0.1 (s, 9); 3.9 (s, 3); 5.5 (s, 1); 7.0 (m, 2); 7.2 (m, 2); 7.9 (s, 1); 7.95 (br, 1); 8.2 (d, 1). | 100-101 |
| 1.46 | | 122-124 |
| 1.47 | | 122-124 |
| 1.56 | | 99-101 |
| 1.57 | | 108-112 |
| 1.58 | | 80-81 |
| 1.59 | | 112-114 |
| 1.60 | | 105-107 |
| 1.61 | | 104-107 |
| 1.62 | | 57-58 |

TABLE 17-continued

| Compound Number | ¹H-NMR data: (ppm/multiplicity/number of Hs) or mass spectrum signal | m.p./(° C.) |
|---|---|---|
| 1.63 | | 134-136 |
| 1.64 | | 135-136 |
| 1.65 | | 139-141 |
| 1.66 | | 124-125 |
| 1.67 | | 80-82 |
| 1.73 | | 83-84 |
| 1.74 | | 86-90 |
| 1.75 | | 90-94 |
| 1.76 | | 46-50 |
| 1.77 | | 101-102 |
| 1.79 | | 88-89 |
| 1.82 | Mass spectrum peak at 316 (M + 1) | |
| 2.1 | | 68-72 |
| 2.3 | −0.1 (s, 9); 2.2 (s, 2); 3.7 (s, 3); 7.1-7.7 (4m, 2, 1, 1, 1); 8.6 (s, 1). | 124-126 |
| 2.7 | −0.1 (s, 9); 1.3 (d, 3); 2.5 (q, 1 coinciding with DMSO signal); 3.7 (s, 3); 7.1-7.35 (m, 3); 7.45 (d, 1); 7.65 (d, 1); 9.3 (s, 1). | 153-155 |
| 2.14 | 0.0 (s, 9); 0.8 (m, 2); 2.6 (m, 2); 3.75 (s, 3); 7.2-7.35 (m, 4); 7.45 (s, 1); 7.65 (s, 1); 9.4 (s, 1). | 118-120 |
| 2.19 | Mass spectrum peak at (M + 1) detected | |
| 2.21 | −0.1 (s, 9); 1.0 (q of d, 2); 1.2 (d, 3); 3.1 (sext, 1); 3.7 (s, 3); 7.0 (sd, 1); 7.2 (m, 2); 7.35 (m, 2); 7.5 (s, br, 1); 7.8 (m, 1). | 147-148 |
| 2.27 | | 107-108 |
| 2.60 | −0.3 (s, 3); −0, 1 (s, 3); 0.8 (s, 9); 0.8-1.1 (m, 2); 1.2 (d, 3); 3.1 (m, 1); 3, 7 (s, 3); 7.0-7.8 (m, 7) | amorphous solid |
| 2.63 | | 84-88 |
| 2.64 | | 135-137 |
| 2.65 | −0.1 (s, 6); 0.7-1.0 (m, 3); 0.9 (d, 6); 2.5 (m, 2); 3.65 (s, 3); 7.0-7.9 (m, 7). | amorphous solid |
| 2.66 | | 115-117 |
| 2.80 | Mass spectrum peak at (M + 1) detected | |
| 2.81 | Mass spectrum peak at (M + 1) detected | |
| 2.67 | | 65-67 |
| 3.3 | 0.0 (s, 9); 2.15 (s, 2); 2.75 (s, 3); 7.1-7.25 (m, 3); 7.35 (dd, 1); 10.2 (s, 1). | 125-128 |
| 3.7 | −0.1 (s, 9); 1.25 (d, 3); 2.5 (q.1 coinciding with DMSO signal); 2.7 (s, 3); 7.1-7.4 (m, 4); 10.3 (s, 1). | viscous oil |
| 3.14 | 0.0 (s, 9); 0.8 (m, 2); 2.6 (m, 2); 2.8 (s, 3); 7.2-7.4 (m, 4); 10.3 (s, 1). | 87-90 |
| 3.18 | Mass spectrum peak at (M + 1) detected | |
| 3.20 | 0.0 (s, 3); 1.0-1.2 (m, 2); 1.3 (d, 3); 2.7 (s, 3); 3.15 (m, 1); 7.2-7.9 (m, 5). | amorphous solid |
| 3.35 | | 85-86 |
| 3.45 | Mass spectrum peak at (M + 1) detected | |
| 3.46 | Mass spectrum peak at (M + 1) detected | |
| 4.14 | | 140-142 |
| 4.20 | | 102-104 |
| 9.3 | 0.0 (s, 9); 2.25 (s, 2); 7.15 (m: 2,); 7.5 (dd, 1); 7.6 (dd, 1); 8.0 (dd, 1); 8.6 (dd, 1); 10.0 (s, 1). | 79-81 |
| 9.14 | 0.0 (s, 9); 0.8 (m, 2); 2.65 (m, 2); 7.2-7.4 (3m: 2, 1, 1); 7.6 (dd, 1); 8.05 (dd, 1); 8.5 (dd, 1); 10.1 (s, 1). | 109-110 |
| 9.19 | 0.0 (s, 9); 1.0 (q of d, 2); 1.35 (d, 2); 3.25 (sext, 1); 7.2-7.5 (2m, 2, 2); 7.8 (m, 1); 8.1 (s, 1). 8.35 (dd, 1); 8.6 (dd, 1). | 78.5-81 |
| 9.35 | | 77-79 |

The compounds according to formula (I) may be prepared according to the following methods.

Some compounds of formula (II) are already known; novel compounds of formula (II) may be prepared according to the following synthetic strategies which are depicted in the following scheme and described below:

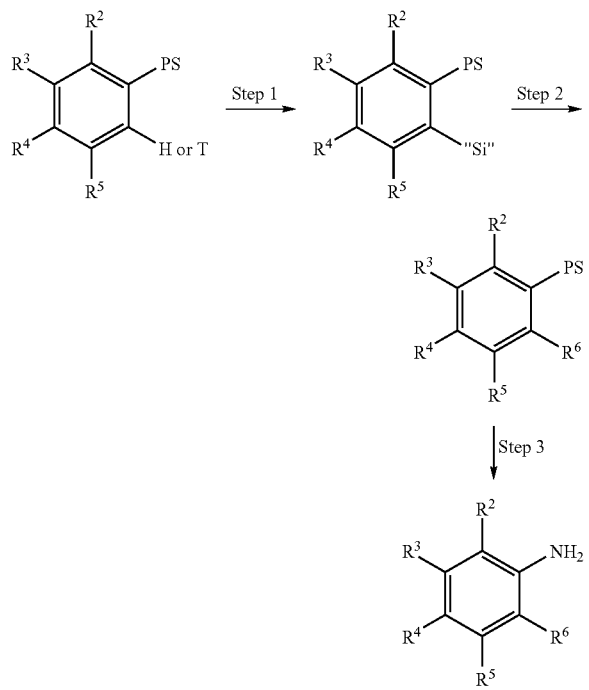

PS = Aminogroup, protected amino or precursor group for amino
T = Functional group convertable to "Si"
"Si" = Silicon containing substituent: R6 or precursor for R6

Step 1: Starting from a suitable precursor carrying a protected or free amino function or a substituent which may be converted to $NH_2$ in a later stage of the synthesis (precursor substituent; PS) and, optionally, a substituent which is convertible to "Si", an appropriate Si-containing functionality ("Si") is introduced into the ortho position.

Step 2: If necessary, the introduced Si-containing group is further manipulated to form the desired substituent $R^6$.

Step 3: Deprotection if necessary or conversion of the precursor substituent to $NH_2$.

Steps 2 and 3 may also be carried out in reversed order.

It is also possible to perform step 1 and 2 on a phenyl derivative which is not substituted in a position ortho to the newly formed $R^6$ (step 1a and 2a) and to introduce the $NH_2$ or the precursor substituent PS afterwards (step 3a) [for example by nitration or via metalation followed by substitution].

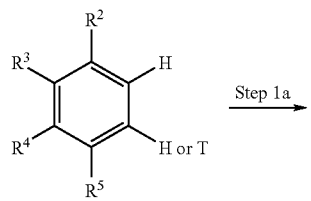

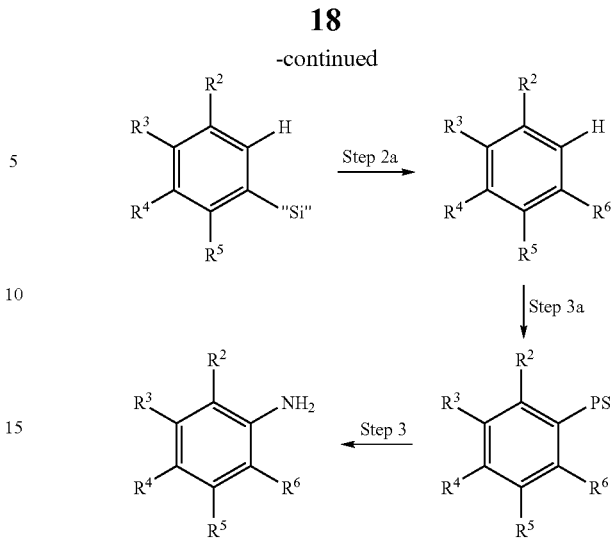

Procedures according to both schemes are exemplified in Examples 1-6.

Literature examples for the nitration of arylsilanes (for the situation where PS is nitro) can be found in E. A. Chernyshev et. al. Izvestiya Akademii Nauk SSSR 8, 1424 (1960) and DE 1114641 (Union Carbide Corp.).

Examples of protecting groups for the $NH_2$ functionality are formyl, acyl, haloacyl, trialkylsilyl, (substituted)benzyl and alkoxycarbonyl. A more comprehensive list of methods for protection and deprotection of anilines which are useful in the context of the present invention can be found in T. W. Green and P. G. M. Wuts, Protective Groups in Organic Synthesis $3^{rd}$ edition p. 503-614 (Wiley 1999).

Examples for precursor substituents PS are nitro and azido [both of which may be converted to $NH_2$ by reduction or hydrogenation], carboxyl and carboxy derivatives [which may undergo rearrangements to form isocyanates, for example by Schmidt- or Hofmann-degradation] and halides and triflates [which may be converted to $NH_2$ in protected or unprotected form via catalytic amination reactions currently known under the name "Buchwald Hartwig" reaction (for example X. Huang et al., Org. Lett. 3, 3417 (2001) and references cited therein)].

More comprehensive lists for useful precursor substituents for $NH_2$ can be found in Rodd's Chemistry of Carbon Compounds III B and its supplements (Elsevier 1974,1981 and 1995) and in Compendium of Organic Synthetic Methods Vols. 1-9 chapter 7 (Wiley 1971-2000).

For the introduction of Si-containing functionalities into phenyl derivatives (step 1) a large variety of synthetic methods are accessible. The chemist skilled in the art will understand that according to the methodology chosen for step 1 different groups T may be used. Examples of useful T substituents are halogens (such as Cl, Br and I), sulfonates (such as triflates, tosylates and mesylates), phosphates, $C_{1-4}$ alkyl, $C_{1-4}$ haloalkyl, $C_{2-4}$ alkenyl, $C_{2-4}$ haloalkenyl, $C_{2-4}$ alkinyl, $C_{1-4}$ alkylcarbonyl and $C_{1-4}$ alkoxycarbonyl.

Manipulation of Si-containing functional groups (step 2) are widely known in the literature. Recent overviews can be found in The Chemistry of Organosilicon Compounds, Vols. 1-3, S. Patay, Z. Rappaport and Z. Rappaport, Y. Apeloid eds. Wiley, 1989, 1998, 2001 and in Houben-Weyl Science of Synthesis, Organometallics Vol. 4, I. Fleming ed., G. Thieme 2002. Examples of such manipulations which are especially relevant to the present invention are hydrogenation or reduction of double or triple bonds (or both) in the Si-containing group (please see later: Example 3, step B), cyclopropanation and epoxidation of said double bonds and functional group manipulation on the silicon atom (for example conversion of halogens to alkyl or alkoxy groups).

Literature examples which illustrate some of the methods which are especially relevant to the preparation of a compound of formula (II) include E. A. Chemyshew et. Al., Bull. Acad. Sci. USSR 1960, 1323; K. T. Kang et. al., TL 32,4341 (1991) Synth. Comm. 24, 1507 (1994); M. Murata et al., TL 40, 9255 (1999); A. Falcou et. al., Tetrahedron 56, 225 (2000); A. Arcadi et al., TL 27, 6397 (1986); K. C. Nicolaou et al., Chem. Eur. J. 1, 318 (1995); N. Chatani et al., JOC 60, 834 (1995); T. Stuedemann et al., Tetrahedron 54, 1299 (1998); P. F. Hurdlik et al., JOC 54, 5613 (1989); K. Karabelas et al., JOC 51, 5286 (1986); T. Jeffery, T L 40, 1673 (1999) and T L 41, 8445 (2000); K. Olofson et. al., JOC 63, 5076 (1998); H. Uirata et al., Bull. Chem. Soc. Jap. 57, 607 (1984); and G. Maas et al., Tetrahedron 49, 881 (1993); and references cited therein.

A compound of formula (I) may be prepared by reacting a compound of formula Het-C(=O)—R* [where Het is as defined above for a compound of formula (I) and R* is halogen, hydroxy or $C_{1-6}$ alkoxy, but preferably chloro] with a compound of formula (II), as defined above, in the presence of a base (such as triethylamine, Hunig base, sodium bicarbonate, sodium carbonate, potassium carbonate, pyridine or quinoline but preferably triethylamine or pyridine) and in a solvent (such as diethylether, TBME, THF, dichloromethane, chloroform, DMF or NMP) for between 10 minutes and 48 hours (preferably 12 to 24 hours) and between 0° C. and reflux (preferably 20 to 25° C.). When R* is chloro, the reaction may also conveniently be carried out by a one-pot procedure by adding a reagent known to chlorinate carboxylic acids [such as thionyl chloride or oxalyl chloride] to a solution of Het-C(=O)—OH [where Het is as defined above for a compound of formula (I)] in an appropriate solvent (preferably diethylether, TBME, THF, dichloromethane, chloroform, tetrachloroethane or hexane) which contains a few drops of DMF as catalyst; removing any excess reagent by evaporation under reduced pressure; and adding the relevant compound of formula (II) and, optionally, more solvent as specified above to the crude heterocyclic acid chloride Het-C(=O)—R* (where R* is chloro). When R* is hydroxy, a coupling agent [such as benzotriazol-1-yloxytris(dimethylamino) phosphoniumhexafluorophosphate, bis-(2-oxo-3-oxazolidinyl)-phosphinic acid chloride, N,N'-dicyclohexylcarbodiimide or 1,1'-carbonyl-diimidazole] may be used. When R* is $C_{1-6}$ alkoxy, a stronger base [such as n-BuLi, LDA or, preferably, hexamethyldisilazanyl-Na (HMDS-Na)] may be used to activate the compound of formula (II).

A compound of formula (I) [where X is S] may be conveniently produced by treating a compound of formula (I) [where X is O] in an appropriate solvent (such as toluene or xylene) with a thionating agent (such as $P_2S_5$ or Lawessons reagent) at elevated temperatures. An example of such a reaction can be found in WO 93/11117.

A compound of formula (I) [where $R^1$ is not hydrogen] may be prepared by: either alkylation or acylation of a compound of formula (I) [where $R^1$ is hydrogen] with a compound $R^dL$ [where $R^d$ is the desired substituent $R^1$ and L is a common leaving group for alkylation or acylation reactions, for example halogen (such as Cl, Br, or I), a sulfonate (such as mesylate or tosylate), a quaternary ammonium group, formyloxy or an acyloxy group]. The reaction is preferably carried out in the presence of a strong base able to deprotonoate the amide function of the compound of formula (I) or in the presence of an acylation catalyst (such as pyridine, a trialkylamine or dimethylaminopyridine) or in the presence of both a strong base and a catalyst. Alternatively a compound of formula (II) may be alkylated or acylated with $R^dL$ [as defined above] and the resulting alkylated or acylated amine is treated with Het-C(=O)—R* as described above.

Surprisingly, it has now been found that the novel compounds of formula (I) have, for practical purposes, a very advantageous spectrum of activities for protecting plants against diseases that are caused by fungi as well as by bacteria and viruses.

The compounds of formula (I) can be used in the agricultural sector and related fields of use as active ingredients for controlling plant pests. The novel compounds are distinguished by excellent activity at low rates of application, by being well tolerated by plants and by being environmentally safe. They have very useful curative, preventive and systemic properties and are used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later e.g. from phytopathogenic microorganisms. It is also possible to use compounds of formula (I) as dressing agents for the treatment of plant propagation material, in particular of seeds (fruit, tubers, grains) and plant cuttings (for example rice), for the protection against fungal infections as well as against phytopathogenic fungi occurring in the soil.

Furthermore the compounds according to present invention may be used for controlling fungi in related areas, for example in the protection of technical materials, including wood and wood related technical products, in food storage, in hygiene management, etc.

The compounds of formula (I) are, for example, effective against the phytopathogenic fungi of the following classes: Fungi imperfecti (e.g. *Botrytis, Pyricularia, Helminthosporium, Fusarium, Septoria, Cercospora* and *Alternaria*) and *Basidiomycetes* (for example *Rhizoctonia, Hemileia, Puccinia*). Additionally, they are also effective against the Ascomycetes classes (for example *Venturia* and *Erysiphe, Podosphaera, Monilinia, Uncinula*) and of the Oomycetes classes (for example *Phytophthora, Pythium, Plasmopara*). Outstanding activity has been observed against powdery mildew (*Erysiphe* spp.). Furthermore, the novel compounds of formula I are effective against phytopathogenic bacteria and viruses (for example against *Xanthomonas* spp, *Pseudomonas* spp, *Erwinia amylovora* as well as against the tobacco mosaic virus).

Within the scope of present invention, target crops to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The compounds of formula (I) are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds may be, for example, fertilizers or micronutrient donors or other preparations which influence the growth of plants. They may also be selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be mixed with other fungicides, resulting in some cases in unexpected synergistic activities. Mixing components which are particularly preferred are azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinole, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydro-phthalimides, such as captafol, captan, dichlofluanid, fluoromides, folpet, tolylfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-5-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

A preferred method of applying a compound of formula (I), or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation [that is, a composition containing the compound of formula (I)] and, if desired, a solid or liquid adjuvant, is prepared in a known manner, typically by intimately mixing and/or grinding the compound with extenders, for example solvents, solid carriers and, optionally, surface active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Advantageous rates of application are normally from 5 g to 2 kg of active ingredient (a.i.) per hectare (ha), preferably from 10 g to 1kg a.i./ha, most preferably from 20 g to 600 g a.i./ha. When used as seed drenching agent, convenient dosages are from 10 mg to 1 g of active substance per kg of seeds.

Whereas it is preferred to formulate commercial products as concentrates, the end user will normally use dilute formulations.

The following non-limiting Examples illustrate the above-described invention in more detail.

EXAMPLE 1

This Example illustrates the preparation of Compound Number 1.14.

2-(2'-Trimethylsilylethyl)aniline (0.5 g) (A. Falcou et. al., Tetrahedron 56, 225 (2000)) and 1-methyl-3-trifluoromethyl-4-chlorocarbonyl-pyrazole (0.55 g) were combined in THF under cooling with ice and then pyridine (0.21 ml) was added. After warming to ambient temperature, the mixture was stirred for 3.5 hours, poured into water and extracted twice with ethylacetate, Separation of the organic phase, drying over sodium sulfate and evaporation of the solvent yielded Compound Number 1.14 (0.9 g; 94.7%).

EXAMPLE 2

This Example illustrates the preparation of Compound Number 2.14.

To 1-methyl-4-trifluoromethyl-pyrrole-3-carboxylic acid (0.5 g) dissolved in dichloromethane (10 ml containing 2 drops of dimethylformamide) thionylchloride (0.24 ml) was slowly added at room temperature. The solution, which soon turned dark, was stirred for 3 hours at room temperature and was then slowly added to a solution of 2-(2' trimethylsilyl-ethyl)aniline (0.5 g) and triethylamine (0.54 ml) in dichloromethane (10 ml) at room temperature. After stirring for 18 hours, the solvent was removed under reduced pressure and the residue taken up in ethylacetate. Washing with water and brine, drying over sodiumsulfate and evaporation of the solvent produced a dark oil (1.08 g), which was purified by flash-chromatography over silica gel (eluent: hexane/ethylacetate 2:1) to yield Compound Number 2.14 (0.3 g; 31.6%).

EXAMPLE 3

This Example illustrates the preparation of Compound Number 1.20.

Step A: Preparation of
2-(2-Nitrophenyl)-3-(trimethylsilyl)-2-propene

2-Iodonitrobenzene [19.7 g] and triethylamine [15.6 ml] were dissolved in dimethylformamide [33 ml]. 1-Trimethyl-silylpropin-1 [4.9 ml] and bis(triphenylphosphin)-palladium-dichloride [1.16 g] were then added at room temperature in a nitrogen atmosphere. After stirring for 5 minutes, formic acid [3.25 ml] was added dropwise. Once the initial exothermic reaction had terminated the mixture was held at 60° C. over night. After cooling, the yellow reaction mixture was poured into a mixture of ethylacetate [350 ml] and water [350 ml], stirred for 1 hour and then the organic phase was collected and washed with water. The product was distilled off under reduced pressure and the residue was purified by chromatography on silicagel (eluent: 5% ethylacetate in hexane) to yield a yellow oil (7.2 g) which was used in the next step without further purification.

Step B: Preparation of
2-(2-Aminophenyl)-3-(trimethylsilyl)-propane

The reaction product of step A [7.2 g] was hydrogenated in tetrahydrofurane over palladium on charcoal at atmospheric pressure and room temperature until the uptake of hydrogen ceased. The catalyst was filtered off and, after evaporation of the solvent, the product was chromatographed on silacagel (eluent: 10% ethylacetate in hexane) to yield 2-(2-aminophenyl)-3-(trimethylsilyl)-propane [4.7 g; 88% purity according to NMR]. This product was used in the next step without further purification.

Step C

To a solution of 2-(2-aminophenyl)-3-(trimethylsilyl)-propane [11 g] and 1-methyl-3-(trifluoromethyl)-pyrazol-4-carbonylchloride [10.15 g] in tetrahydrofuran [150 ml], pyridine [3.85 ml] was added whilst cooling with ice. The mixture was stirred at ambient temperature over night to give a yellow suspension. The solvent was evaporated under reduced pressure and then water and ethylacetate were added and the organic phase was collected, washed with saturated brine and dried. Evaporation of the solvent yielded Compound Number 1.20 which was recrystallised from a mixture of hexane and toluene. Yield: 13.55 g.

EXAMPLE 4

This Example illustrates the preparation of Compound Number 2.20.

2-(2-Aminophenyl)-3-(trimethylsilyl)-propane (25 g; purity 85%), 1-methyl-3-(trifluoromethyl)-pyrrole-4-carboxylic acid [19.8 g] and triethylamine [28.6 g] were dissolved in dichloromethane [500 ml] and then bis(2-oxo-3-oxazolidinyl)phoshinicacid chloride [26.1 g] was added with ice cooling. The reaction mixture was allowed to warm to room temperature and stirred overnight. Most of the solvent was evaporated under reduced pressure and then the residue was diluted with ethylacetate [1000 ml] and twice washed with saturated sodiumbicarbonate solution and brine. After drying with sodium sulfate the solvent was evaporated to yield crude Compound Number 2.20; recrystallisation from hexane and toluene yielded 14.1 g of the desired product.

EXAMPLE 5

This Example illustrates the preparation of Compound Number 9.35.

2-Trimethylsilyl-3-phenylpropene (2.5 g), prepared according to J. Org. Chem. 43, 147 (1978), was dissolved in THF and was then hydrogenated over Pd on charcoal under atmospheric pressure and at room temperature until the uptake of hydrogen ceased. Removal of the catalyst and the solvent yielded an oil (2.36 g) which was chromatographed on silica gel (eluent: hexane:ethylacetate 39:1) to give 2-trimethylsilyl-3-phenylpropane (2.3 g; 92.5% pure by NMR). This compound was dissolved in acetanhydride (4 ml), cooled to −35° C. and at this temperature a pre-cooled mixture of concentrated nitric acid (0.48 ml) and acetanhydride (2.4 ml) was added slowly. After warming to ambient temperature the reaction mixture was stirred for 3 hours and then poured into ice-cold diluted ammonia. After extraction with ethyl acetate and drying over sodium sulfate the solvent was removed and the residue was chromatographed on silica gel (eluent:hexane: THF:ethylacetate 39:4:1) added) to yield a yellow oil (1.4 g) which consisted of an approximate 1:1 mixture of 2-trimethylsilyl-3-(2'-nitrophenyl)-propane and 2-trimethylsilyl-3-(4'-nitrophenyl)-propane. This mixture was hydrogenated over Pd on charcoal under atmospheric pressure and at room temperature until the uptake of hydrogen ceased. Removal of the catalyst and the solvent and chromatography on silica gel (eluent: hexane:ethyl acetate, 4:1) yielded 2-trimethylsilyl-3-(2'-aminophenyl)-propane (0.75 g; pure according to NMR). 0.15 g of this compound was dissolved in dry THF, cooled with ice and 2-chloronicotinoylchloride (0.13 g) was added, followed by pyridine (0.01 ml). The reaction mixture was stirred at room temperature over night, poured on to water and extracted twice with ethylacetate. The organic phase was washed with water, dried with sodium sulfate and the solvent was removed. Recrystallisation of the resulting crystals from hexane yielded Compound Number 9.35 (0.16 g).

EXAMPLE 6

This Example illustrates the preparation of Compound Numbers 1.62 and 1.64.

Step A: Preparation of 2-(2'
aminophenyl)-3-dimethylethylsilyl-propen-1

To n-butyllithium (56.3 ml; 1.6M in hexane) at 0° C. potassium tert-butoxide (3.37 g) was added in 3 portions over 20 minutes. At the same temperature 2-isopropenylaniline (4 g) dissolved in hexane (4 ml) was added. The temperature rose to approximately 9° C. and stirring was continued for another 2 hours while keeping the temperature at 0° C. The reaction was quenched by adding diethylchlorosilane (12.6 ml). After warming to room temperature the reaction mixture was stirred with saturated ammoniumchloride solution (200 ml), twice extracted with ethylacetate and the organic phase was washed with brine. After drying with sodium sulfate the solvents were stripped off and the resulting yellow oil was chromatographed over silica gel (eluent: hexane:ethylacetate 19:1) to yield the desired product (1.2 g) which was pure enough according to nmr to be used in step B.

Step B: Preparation of Compound Number 1.62

The product of step A (0.3 g) was treated with 1-methyl-3-trifluoromethyl-4-chlorocarbonyl-pyrazole (0.29 g) in an analogous manner to that described in Example 1, to yield Compound Number 1.62 (0.44 g).

Step C: Preparation of 1-(dimethylethylsilyl)-2-(2' aminophenyl)-propane

The product of step A (0.85 g) was hydrogenated as described in Example 3, Step B to yield, after chromatography on silica gel (eluent: hexane:ethylacetate 19:1), of the desired aniline (0.72 g) which was characterized by NMR.

Step D: Preparation of Compound Number 1.64

The product of step C (0.35 g) was treated with 1-methyl-3-trifluoromethyl-4-chlorocarbonyl-pyrazole (0.34 g) in an analogous manner to that described in Example 1, to yield Compound Number 1.64 (0.51 g).

Formulation Examples for Compounds of Formula (I)

Working procedures for preparing formulations of the compounds of formula I such as Emulsifiable concentrates, Solutions, Granulates, Dusts and Wettable powders are described in WO 97/33890.

BIOLOGICAL EXAMPLES

Fungicidal Actions

Example B-1

Action Against *Puccinia recondite*/Wheat (Brownrust on Wheat)

1 week old wheat plants cv. Arina are treated with the formulated test compound (0.02% active ingredient) in a spray chamber. One day after application wheat plants are inoculated by spraying a spore suspension ($1 \times 10^5$ uredospores/ml) on the test plants. After an incubation period of 2 days at 20° C. and 95% r. h. plants are kept in a greenhouse for 8 days at 20° C. and 60% r.h. The disease incidence is assessed 10 days after inoculation.

Infestation is prevented virtually completely (0-5% infestation) with each of Compounds 1.1, 1.2, 1.14, 1.16, 1.17, 1.21, 1.21B, 1.24, 1.26, 1.27, 1.32, 1.46, 1.47, 1.56, 1.57, 1.60, 1.62, 1.63, 1.64, 1.66, 1.67, 1.73, 1.77, 1.79, 2.1, 2.14, 2.21, 2.27, 2.60, 2.63, 2.66, 2.67, 3.14, 3.20, 4.20, 9.14 and 9.19.

Example B-2

Action Against *Podosphaera leucotricha*/Apple (Powdery Mildew on Apple)

5 week old apple seedlings cv. McIntosh are treated with the formulated test compound (0.002% active ingredient) in a spray chamber. One day after application apple plants are inoculated by shaking plants infected with apple powdery mildew above the test plants. After an incubation period of 12 days at 22° C. and 60% r.h. under a light regime of 14/10 hours (light/dark) the disease incidence is assessed.

Compounds 1.1, 1.2, 1.3, 1.14, 1.16, 1.21, 1.21B, 1.24, 1.27, 1.46, 1.64, 1.67, 1.73, 1.77, 2.3, 2.14, 2.27, 2.63, 3.3, 3.14, 3.20, 9.3, 9.14 and 9.19 each exhibit strong efficacy (<20% infestation).

Example B-3

Action Against *Venturia inaequalis*/Apple (Scab on Apple)

4 week old apple seedlings cv. McIntosh are treated with the formulated test compound (0.02% active ingredient) in a spray chamber. One day after application apple plants are inoculated by spraying a spore suspension ($4 \times 10^5$ conidia/ml) on the test plants. After an incubation period of 4 days at 21° C. and 95% r.h. the plants are placed for 4 days at 21° C. and 60% r.h. in a greenhouse. After another 4 day incubation period at 21° C. and 95% r.h. the disease incidence is assessed.

Compounds 1.2, 1.14, 1.16, 1.21, 1.21B, 1.24, 1.27, 1.32, 1.46, 1.63, 1.64, 1.77, 1.79, 2.14, 2.27, 2.63, 3.14 and 9.14 each exhibit strong efficacy (<20% infestation).

Example B-4

Action Against *Erysiphe graminis*/Barley (Powdery Mildew on Barley)

1 week old barley plants cv. Express were treated with the formulated test compound (0.02% active ingredient) in a spray chamber. One day after application barley plants were inoculated by shaking powdery mildew infected plants above the test plants. After an incubation period of 6 days at 20° C./18° C. (day/night) and 60% r.h. in a greenhouse the disease incidence was assessed.

Compounds 1.1, 1.2, 1.14, 1.16, 1.17, 1.21, 1.21B, 1.24, 1.26, 1.27, 1.60, 1.63, 1.64, 1.66, 1.73, 1.67, 1.79, 2.1, 2.14, 2.27, 2.60, 2.63, 2.65, 3.14, 3.20, 9.14 and 9.19 each exhibit strong efficacy (<20% infestation).

Example B-5

Action Against *Botrytis cinerea*/Tomato (*Botrytis* on Tomatoes)

4 week old tomato plants cv. Roter Gnom were treated with the formulated test compound (0.02% active ingredient) in a spray chamber. Two days after application tomato plants were inoculated by spraying a spore suspension ($1 \times 10^5$ conidia/ml) on the test plants. After an incubation period of 4 days at 20° C. and 95% r.h. in a growth chamber the disease incidence was assessed.

Compounds 1.3, 1.14, 1.16, 1.46, 1.47, 1.63, 2.1, 2.3, 2.14, 2.63, 3.3, 3.14, 9.3 and 9.14 each exhibit strong efficacy (<20% disease incidence).

Example B-6

Action Against *Septoria nodorum*/Wheat (*Septoria* Leaf Spot on Wheat)

1 week old wheat plants cv. Arina were treated with the formulated test compound (0.02% active ingredient) in a spray chamber. One day after application wheat plants were inoculated by spraying a spore suspension ($5\times10^5$ conidia/ml) on the test plants. After an incubation period of 1 day at 20° C. and 95% r.h. plants are kept for 10 days at 20° C. and 60% r.h. in a greenhouse. The disease incidence was assessed 11 days after inoculation.

Compounds 1.21B, 1.24, 1.32, 1.46, 1.47 and 1.56 each show good activity in this test (<60% disease incidence).

The invention claimed is:

1. A compound of formula (II):

(II)

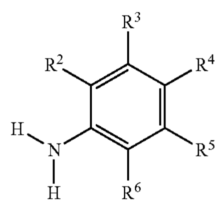

where $R^2$, $R^3$, $R^4$ and $R^5$ are each, independently, hydrogen, halogen, $CH_3$, $CF_3$ or $OCF_3$; $R^6$ is $(CHR^{10})(CR^{11}R^{12})_rSi(R^{13})(R^{14})(R^{15})$; $_{r\ is}$ 1, 2 or 3; $R^{10}$ is $C_{1-3}$ alkyl or $C_{1-3}$ haloalkyl; and when each $R^{11}$ and each $R^{12}$ is, independently, chosen from hydrogen, halogen, $C_{1-3}$ alkyl and $C_{1-3}$ haloalkyl; or $R^{10}$ and $R^{11}$ on adjacent carbon atoms or two $R^{11}$ on adjacent carbon atoms may together be a double bond; $R^{13}$ and $R^{14}$ are each, independently, methyl or ethyl; and $R^{15}$ is $C_{1-6}$ alkyl, $C_{1-4}$ alkoxy($C_{1-4}$)alkyl, $C_{1-3}$ haloalkyl, $C_{2-6}$ alkenyl or $C_{1-6}$ alkoxy; provided that $R^6$ is such that its total number of carbon atoms is 6-13, its total number of halogen atoms is 0-4 and its total number of heteroatoms is 0-3.

2. A compound according to claim 1, wherein $R^{10}$ is methyl.

3. A compound according to claim 1, wherein $R^{11}$ is hydrogen or methyl.

4. A compound according to claim 1, wherein $R^{12}$ is hydrogen or methyl.

5. A compound according to claim 1, wherein $R^{13}$ is methyl.

6. A compound according to claim 1, wherein $R^{14}$ is methyl.

7. A compound according to claim 1, wherein $R^{15}$ is Me, Et, $CHMe_2$, $CH_2CH_2Me$, $CH_2CHMe_2$, OMe, $OCHMe_2$ or $OCH_2CHMe_2$.

8. A compound according to claim 1, wherein $R^6$ is CHMeC $H_2$ $SiMe_3$, $CHMeCH_2SiMe_2Et$, $CHMeCH_2SiMe_2CHMe_2$, $CHMeCH_2SiMe_2CMe_3$, $CHMeCH_2SiMe_2CH_2CHMe_2$, $CFMeCH_2SiMe_3$, $CHMeCH_2CH_2SiMe_2OMe$, $CHMeCH_2SiMe_2OCHMe_2$, $CHMeCH_2SiMe_2OCH_2CHMe_2$, $CHMeCH_2CH_2SiMe_3$, $CHMeCH_2CH_2SiMe_2Et$, $CHMeCH_2CH_2SiMe_2CHMe_2$, $CHMeCH_2CH_2CH_2SiMe_2OMe$, $CHMeCH_2CH_2SiMe_2OCHMe_2$, or $(CHMe)_2SiMe_3$.

* * * * *